United States Patent [19]

Bhanumati et al.

[11] 4,354,033

[45] Oct. 12, 1982

[54] ANTHRANILIC ACID ESTERS

[75] Inventors: Nanduri Bhanumati; Pralhad B. Sattur, both of Hyderabad, India

[73] Assignee: Council of Scientific & Industrial Research, New Delhi, India

[21] Appl. No.: 298,247

[22] Filed: Aug. 31, 1981

[51] Int. Cl.³ .................. C07C 101/54; A61K 31/245
[52] U.S. Cl. ........................................ 560/48; 560/45; 560/46; 560/47; 424/230; 424/310
[58] Field of Search ........................ 560/45, 47, 48, 46

[56] References Cited
U.S. PATENT DOCUMENTS 3,313,848  4/1967  Scherrer et al. ...................... 560/48
3,852,333  12/1974  Fisher .................................... 560/48
4,135,050  1/1979  Hess et al. ............................. 560/47

FOREIGN PATENT DOCUMENTS 1199386  7/1970  United Kingdom .................. 560/48

Primary Examiner—G. T. Breitenstein
Attorney, Agent, or Firm—Holman & Stern, Chartered

[57] ABSTRACT

Anthranilic acid esters having the generic formula:

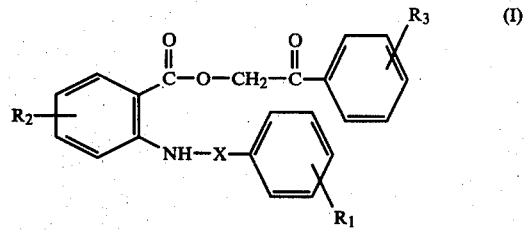

have been discovered. In the above formula (I) $R_1$, $R_2$ and $R_3$ represent any of hydrogen, chlorine, methoxy and methyl groups and X represents a straight or branched alkyl chain comprising 1 to 4 carbon atoms. These esters are anti-inflaments, blood platelet aggregation inhibitors and prostaglandin synthetase inhibitors.

The compounds of the above formula (I) may be prepared by reacting alkali metal salt of a compound of the formula (II):

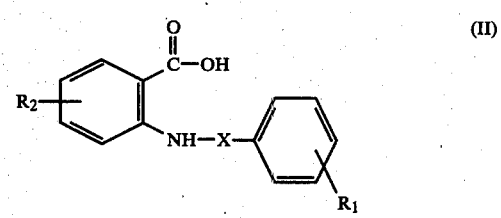

in which $R_1$, $R_2$, $R_3$ and X are the same as before with the compound of formula (III):

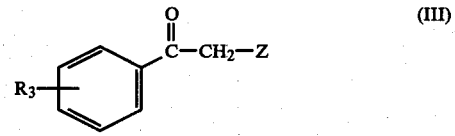

in which $R_3$ has the same meaning as before and z represents a chlorine or a bromine radical.

4 Claims, No Drawings

ANTHRANILIC ACID ESTERS

This invention relates to novel anthranilic acid esters having the general formula (I):

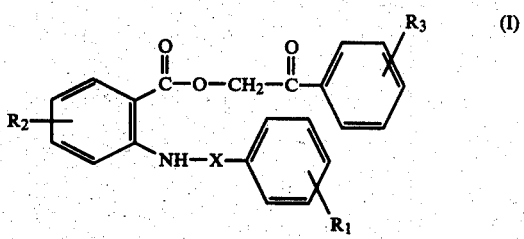

in which $R_1$, $R_2$ and $R_3$ represent any of hydrogen, chlorine, methoxy and methyl groups and X represents a straight or branched alkyl chain comprising 1 to 4 carbon atoms.

The compounds of this invention are anti-inflaments, blood platelet aggregation inhibitors and prostaglandin synthetase inhibitors.

As representative members of the compounds of the above formula following examples are given:

(1) 2-N-β-phenethyl-phenacyl anthranilate of the formula (IV):

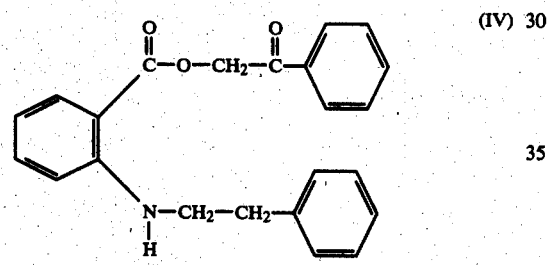

(2) 2-N-β-phenethyl-4-methoxy phenecyl anthranilate of the formula (V):

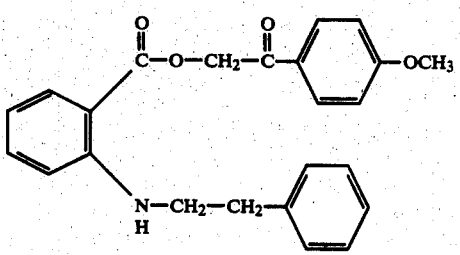

(3) 2-N-β-phenethyl-4′-methyl phenacyl anthranilate of the formula (VI):

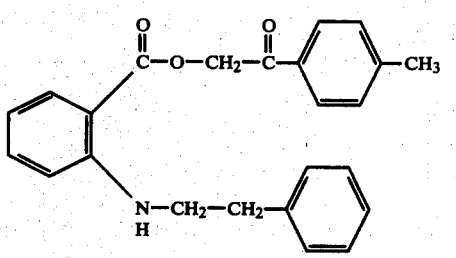

(4) 2-N-β-phenethyl-4′-chlorophenacyl anthranilate of the formula (VII):

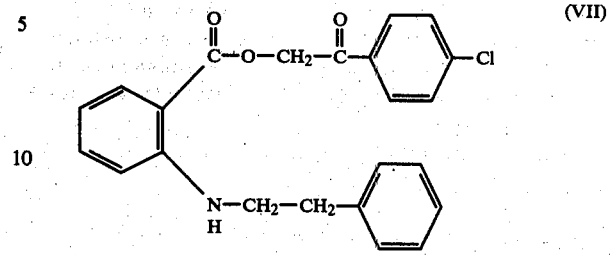

This invention also relates to a process for preparing anthranilic acid esters of the formula I as defined hereinbefore.

Compounds of this invention (represented by the general formula I) may be prepared by reacting an alkali metal salt of compounds of the general formula:

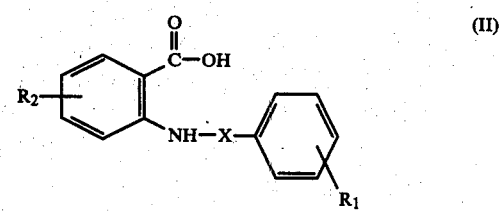

wherein $R_1$, $R_2$ and X have the same meaning as stated above with a compound of the formula:

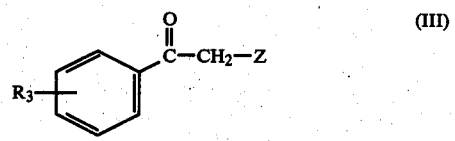

wherein $R_3$ has the same meaning as stated above and Z represents a halogen atom. The reaction is carried out by refluxing the reactants in an organic solvent. The preferred solvent is an aliphatic ketone. The mixture is refluxed at the boiling point of the solvent employed.

As alkali metal salts may be used the sodium or potassium salts.

Solvents employed may be acetone or a higher boiling aliphatic ketone.

The reaction is carried out by refluxing the mixture for from 60 to 240 minutes.

The following examples of the process of preparing a few compounds of this invention are given by way of illustration only and are not to be regarded as limitative of the invention scope of which is to be determined by the appended claims.

EXAMPLE 1

2-N-β-phenethyl-phenacyl anthranilate (IV)

In a round bottomed flask fitted with a condensor, 15 gm. of sodium salt of N-β-phenethylanthranilic acid was taken, α-chloroacetophenone (8 gm) in 85 ml of acetone was added. The reaction mixture was refluxed for about 4 hours. After removal of the solvent the mixture was poured in ice-water. It was filtered and recrystalised from ethanol.

Yield: 85 percent; M.P. 120° C.

EXAMPLE 2

2-N-β-phenethyl-4'-methoxy phanacyl anthranilate (V)

Following the same procedure as in Example 1, 15.0 gm Sodium N-β-phenylethyl anthranilate was reacted with 12.0 gm of 4'-methoxy-α-bromoacetophenone in 100 ml of acetone. Time for which reactants were refluxed was 200 minutes.

Yield: 80 percent; M.P. 103° C.

EXAMPLE 3

2-N-β-phenethyl-4'-methyl phenacyl anthranilate (VI)

This was prepared by refluxing 15.0 gm of sodium N-β-phenethyl anthranilate in a solution containing 11.0 gm of 4'-methyl-α-chloroacetophenone in 100 ml of acetone for 180 minutes.

After removal of the solvent the mixture was poured in ice-water, filtered and re-crystallised from ethanol.

Yield: 80 percent; M.P. 105° C.

EXAMPLE 4

2-N-β-phenethyl-4'-cholorophenacyl anthranilate (VII)

Same method as in Example 3 was followed using 15.0 gm of sodium N-β-phenethyl anthranilate and 12.0 gm. of 4'-chlorobromoacetophenone dissolved in 120 ml of acetone.

Yield: 80 percent; M.P. 115° C.

The structure of the compounds has been arrived at by elemental analysis and spectroscopic evidence.

Pharmaceutical activity of these compounds has been studied and given below are the typical results of study of such activity in respect of 2-N-β-phenethyl phenacyl anthranilate:

This compound has a $LD_{50}$ value of more than 800 mg/kg i.p mice and has potent anti-inflammatory activity as evident from the following observation in a batter of tests:

Antiinflammatory action (Rats): Dose: 100 mg/kg p.o.

(i) It produces 44.5% inhibition when given, one hour before the injection of carrageenin.
(ii) It produces 30% inhibition when given ½ hour before the injection of carrageenin.
(iii) 43% inhibition was observed when given ½ hour after the injection of carrageenin.

Effect on carrageenin oedema at 200 mg/kg (p.o.)

(i) 60% inhibition when given 1 hour before the injection of carrageenin.
(ii) 43% inhibition when given ½ hour before the injection of carrageenin.
(iii) 62% of inhibition when given ½ hour after the injection of carrageenin.

Antiinflammatory action (Rats)

(i) It produces 44.5% inhibition in a dose of 100 mg/kg given orally, one hour before the injection of carrageenin.
(ii) It produces 30% inhibition when given ½ hour before the injection of carrageenin.
(iii) 43% inhibition was observed when given ½ hour after the injection of carrageenin.

Effect on carrageenin oedema at 200 mg/kg (i) 60% inhibition when given 1 hour before the injection of carrageenin.
(ii) 43% inhibition when given ½ hour before the injection of carrageenin.
(iii) 62% of inhibition when given ½ hour after the injection of carrageenin.

Formaldehyde Arthritis

It produces 14% inhibition of formaldehyde induced arthritis when administered orally daily in a dose of 100 mg/kg for 10 days.

Cotton Pellet Granuloma

It shows 31% inhibition of cotton pellet granuloma when given orally daily at 100 mg/kg for 7 days.

Mouse Capillary Permeability: at 100 mg. gives 52% inhibition.

Ulcerogenic Properties

The compound does not show any ulcerogenic activity when administered orally for 7 days in a dose of 100 mg/kg daily.

What is claimed is:

1. Anthranilic acid esters having the general formula:

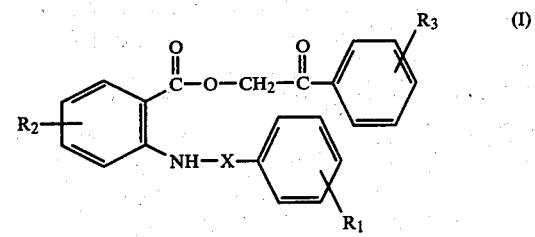

in which $R_1$, $R_2$ and $R_3$ represent any of hydrogen, chlorine, methoxy and methyl groups and X represents a straight or branched alkyl chain comprising 1 to 4 carbon atoms.

2. 2-N-β-phenethyl-4'-methoxy phenacyl anthranilate.
3. 2-N-β-phenethyl-4'-methyl phenacyl anthranilate.
4. 2-N-β-phenethyl-4'-chlorophenacyl anthranilate.

* * * * *